United States Patent [19]
Hacker

[11] Patent Number: 5,452,721
[45] Date of Patent: Sep. 26, 1995

[54] SCANNING GAMMA CAMERA INCLUDING A SYSTEM FOR CONTROLLING THE SPATIAL LIMITS OF THE SCAN

[75] Inventor: Yigal Hacker, Haifa, Israel

[73] Assignee: Elscint Ltd., Haifa, Israel

[21] Appl. No.: 206,282

[22] Filed: Mar. 7, 1994

Related U.S. Application Data

[63] Continuation of Ser. No. 894,342, Jun. 4, 1992, abandoned.

[30] Foreign Application Priority Data

Jun. 9, 1991 [IL] Israel ............................ 098419

[51] Int. Cl.⁶ .................................................. A61B 6/00
[52] U.S. Cl. ..................... 128/659; 5/601; 250/363.02
[58] Field of Search .............................. 128/653.1, 653.2, 128/659; 250/363.02; 5/600, 601

[56] References Cited

U.S. PATENT DOCUMENTS 4,131,802  12/1978  Braden et al. ............... 250/363.02

*Primary Examiner*—Ruth S. Smith
*Attorney, Agent, or Firm*—Sandler, Greenblum & Bernstein

[57] ABSTRACT

A system for controlling the scan limits of a gamma camera during a whole body scan regimen wherein the limits are set by controls at the patient bed.

5 Claims, 1 Drawing Sheet

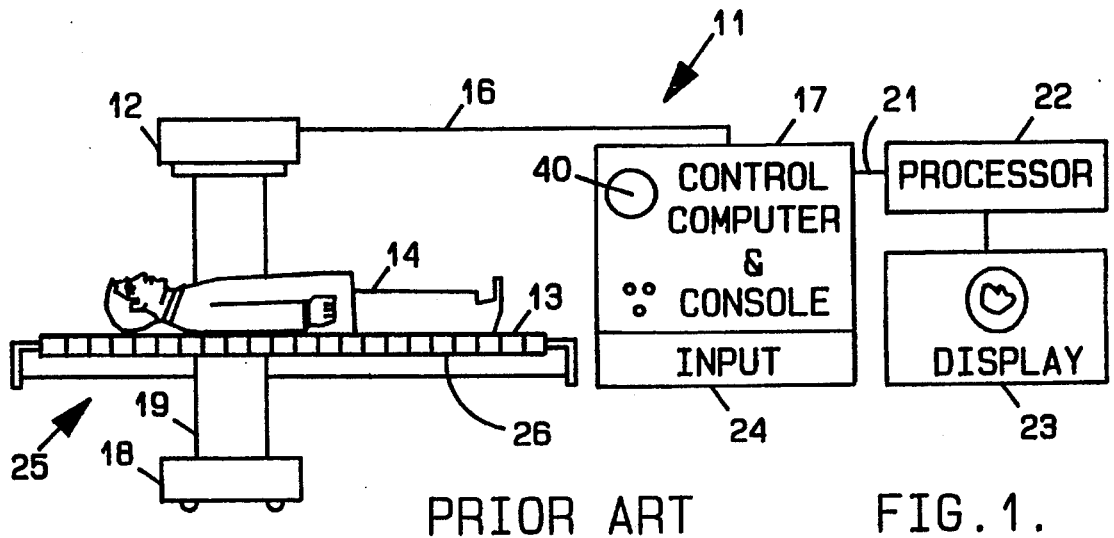
PRIOR ART FIG.1.
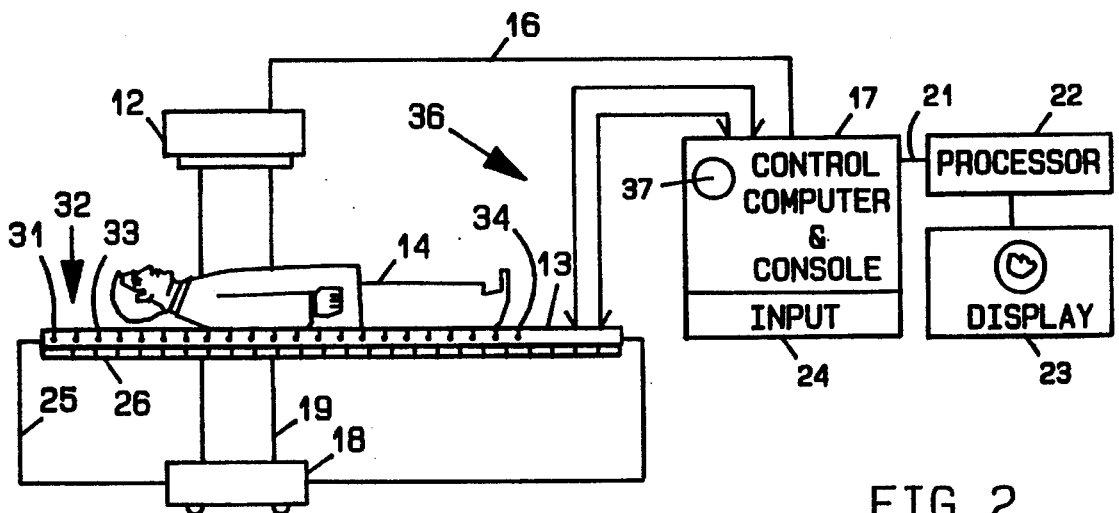
FIG.2.
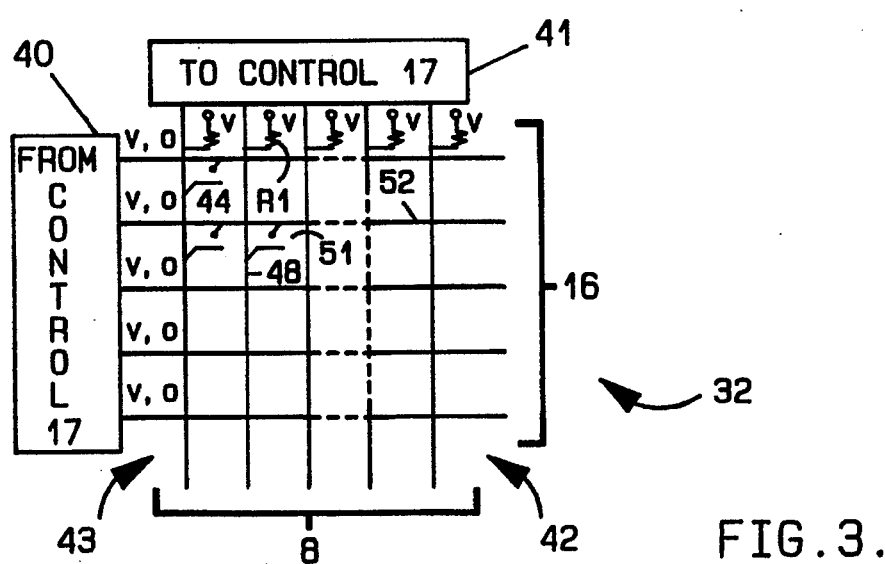
FIG.3.

SCANNING GAMMA CAMERA INCLUDING A SYSTEM FOR CONTROLLING THE SPATIAL LIMITS OF THE SCAN

This application is a continuation of application Ser. No. 07/894,342, filed Jun. 4, 1992, now abandoned.

FIELD OF THE INVENTION

This invention is concerned with diagnostic imaging systems such as gamma camera systems and more particularly with means associated with the patient bed in such systems for controlling the spatial limits of scans of the patient.

BACKGROUND OF THE INVENTION

Diagnostic imaging systems non-invasively obtain images of the patient's interior. Scanning gamma cameras are used, for example, to image patients with bone cancer in order to determine whether or not the disease has metastasised and spread to other organs. Scans are normally carried out with conventional gamma cameras coupled to a mechanical arrangement for establishing relative movement between the camera head and the patient bed carrying the patient. The scan of a radiation field emitted by the patient after the ingestion of a particular radio isotope is usually carried out in a single or a multiple pass mode of operation. In either case, the scanning gamma camera passes from one longitudinal end of the patient to the other and for multiple scans, back again.

It is the usual practice in the prior art for the operator of the gamma camera system to walk over to the patient bed which is provided with a ruler for visually determining the limits of the scan. Thus, the scanning camera gantry control may be programmed to start a scan at position 5 on the ruler and end the scan at position 75. (The 5 and 75 being units of length). To program in this information in the prior art, the operator goes over to the bed, looks at the ruler and then goes back to the control computer console and inputs the beginning and end scan information into the control console. The scanning camera then automatically moves to the start position, starts its scan and continues to scan to the end position.

This prior art method of informing the scanning camera where to begin the scan and where to end the scan is not only time consuming, but also increase the probability for error. Thus, as often happens, the operator may be distracted on the way from the bed to the console and is liable to insert the wrong information into the control computer. Thus, the scan would have to be repeated with the proper information.

More important than the chance of error is the general inefficiency of going to the table and returning to the console to input the information. It is necessary for the operator to go to the patient bed in order to make sure that everything is alright. For example, he makes sure that cables and general equipment are clear for the scanning operation. He also notes where he wants the scan to start and to end. He then returns to the console and inputs the information. However, as mentioned hereinbefore, the necessity of returning to the console before inputting the scan information is inefficient.

BRIEF DESCRIPTION OF THE INVENTION

In accordance with the present invention, a diagnostic imaging system is provided which comprises:

a bed for supporting a patient thereon, a radiation detector for performing a scan of said patient supported on the bed to acquire imaging data, limit controls is for controlling the radiation detector to define the longitudinal movement of the spatial limits of the scan, and switches associated with the bed to supply the spatial limits to the limit controls.

According to a more particular embodiment of the invention, a scanning gamma camera system is provided, said system comprising:

radio isotopes ingested by said patient generate a radiation field, a detecting head for providing electrical signals responsive to said radiation field, controls for causing the head to follow a scan regimen wherein the read scans the patient going from a beginning scan limit of the patient to an end scan limit of the patient, and means associated with said bed to provide said scan limits to said controls from said bed.

A related feature of the invention includes an encoder operated by the operator from the bed to position the scan limits as desired. The encoder converts the desired limits to signals for inputting into the controls means to enable the control means to cause the scan to begin at a desired limit and to end the scan at a desired limit.

More particularly, when the operator goes to the bed he marks on a ruler having switches associated therewith where he wants the scan to begin and where he wants the scan to end. The operation of the switches at those positions notifies the control means of the scan limits. Thus, the scanning gamma camera spatial limit control enables operating the scan regimen more efficiently and reduces the probabability of errors in the scan regimen.

A further feature of the invention uses a keyboard matrix, well known to those skilled in the art, as the encoder.

The above mentioned and other objects and features of the invention will be best understood by considering the following description of preferred embodiment of the invention in relation to the accompanying drawings; wherein:

FIG. 1 is a block diagram showing of a prior art scanning gamma camera,

FIG. 2 shows in block diagram form the inventive scanning gamma camera, and

FIG. 3 is an example of a location encoder for use with the scanning gamma camera of FIG. 2.

GENERAL DESCRIPTION

The scanning gamma camera's system 11 of the prior art includes a gamma camera head shown at 12 mounted above the patient bed 13 having a patient 14 thereon. The patient has ingested a radioactive isotope and, therefore, is a source of a radioactive field emitting gamma radiation. The detector head 12 generally receives the gamma radiation in a scintillating crystal which scintillates responsive to impact of gamma radiation with the crystal. The light scintillation is converted by photomultipliers into electrical signals within the head in a well known manner. An example of a scanning gamma camera is to be seen in U.S. Pat. No. 4,432,059 which issued on Feb. 14, 1984, and is assigned to the Assignee of this invention.

The electrical signals are passed by cables, such as cable 16, to control computer 17. The control computer controls the scanning operation by causing relative movement between the scanning gamma camera head 12 and the patient bed 13. For example, a scanning gamma camera 12 is mounted on pedestal 18 by a standard 19. The pedestal is equipped to move relative to the bed in any well known manner. Within the scope of the invention, of course, the bed can also move relative to the gamma camera. The electrical signal from the gamma camera is carried by cable 16 to the control computer and from there over cable 21 to an image processor 22. The image processor determines the energy of the signals received and the location of the events; i.e., location of the impact of the gamma radiation with the scintillation crystal to provide information for the image display in display means 23.

Means are provided for inputting information to the control computer. More particularly, for example, keyboard 24 is provided. The input information, among other things, determines the details of the regimen to be followed during the scan sequence. Thus, included in the input information required is the beginning location of the scan and the final scan location; i.e., the spatial limits of the scan.

In the prior art a ruler such as ruler 26 was attached to the bed 13. The operator while at the site of the scan noted the ruler designation of the beginning of the scan and the ruler designation of the end of the scan. He then went back to the control computer input 24 and input this information into the control computer. During the scan then, the gamma camera 12 started at the beginning point and took the scan to the end point signified by the operator.

FIG. 2 shows the inventive scanning gamma camera control. The same reference numerals are used in FIG. 2 as were used for the same parts in FIG. 1. FIG. 2 shows all of the same parts that were in FIG. 1; that is the scanning gamma camera 12, the bed 13 holding the patient 14, the cable 16 for conducting the signals from the scanning gamma camera to the control computer 17. The conductors 21 for carrying the signals from the control computer to the image procesor 22 for providing a display in the display means 23. The input 24 into the control computer 17 is also provided.

It should be noted that the scanning gamma camera 12 in FIG. 2 also is mounted onto a base 18 through a standard 19. Mechanical means generally indicated as 25 in both FIGS. 1 and 2 are used to move the bed relative to the scanning camera or the scanning camera relative to the bed in both FIGS. 1 and 2.

The difference between FIG. 1 and FIG. 2 lies in the scan spatial limit encoder 31 shown in FIG. 2 mounted onto the side of the bed 13 along with the ruler 26. More particularly, as shown in FIG. 2, there is the limit encoder 31 shown as including a plurality of switches 32 aligned with the ruler means 26. Actually the ruler may be omitted. When the operator comes to the bed 13, he notes the limits of the scan that are required by operating the switches such as, for example, switch 33 and switch 34 of the plurality of switches 32. This encodes the limits for the scan for inputting into control computer 17 over bus 36.

The operator returns to the control computer, notes that the start limit and the end limit of the scan as shown on the control computer control CRT 37 are the ones that he has selected. Thus, it is not necessary in the inventive system of FIG. 2 for the operator to come back to the control console and input the limits of the scan. They are input while he is standing beside the bed to assure that the proper instructions are input into the control computer and console 17.

Within the scope of the invention, any system or device well known to those skilled in the art can be used for encoding the input and output limits of the scan.

FIG. 3 shows one preferred embodiment of the encoder 31. The embodiment shown is keyboard type encoder. The keyboard encoder has an input from control computer 17 shown at 40 and an output to control computer 17 at 41. The encoder 31 is in the form of a crossbar switch having rows 42 and columns 43. There are switches such as switch 44 at each of the points of crossover of the rows and columns. When a switch is closed, the particular associated row and column are connected together. Each column has a voltage applied thereto through a limiting resistor. For example, column 48 has a voltage V applied through resistor R1.

The input to the rows from the control computer 17 are voltages except for one of the rows onto which the input is zero. The zero input is short lived. It is replaced by a voltage and the zero input is then applied to the next succeeding row. When the switch 51 is closed, it remains closed long enough for the zero to be applied to row 52. The control computer 17 detects the zero at column 48 during the time period when zero is applied to row 52. It detects from this information that switch 51 has been operated. The closure of switch 51 indicated a location along the bed. In a a preferred embodiment, there are eight columns and 16 rows or 128 switches. The first switch operated indicates the start position of the scan, the next switch operated indicates the end position of the scan.

Thus, in practice, the spatial limit encoder in the diagnostic imaging system makes the system much more efficient and enables the operator to put in the scan limits while standing next to the patient on the patient bed.

It is believed that the advantages in improved results furnished by the system of the present invention are apparent from the foregoing description of the preferred embodiment of the invention. Various changes and modifications may be made without departing from the spirit and scope of the invention as described in the claims that follow:

What is claimed is:

1. A scanning gamma camera system for imaging a patient that has ingested radioisotopes to provide medical diagnostic images of the interior of the patient by processing data obtained from a radiation field emanating from the patient due to the ingested radioisotopes, said system comprising:

a bed adapted to support the patient during said imaging, a gamma camera detector head mounted to move relative to the bed to scan the patient on the bed, said gamma camera detector head providing electrical signals responsive to said radiation field as said gamma camera head scans the patient, controls for causing the gamma camera head to follow a scan regimen in which the head moves relative to the bed from one limit of the scan to another limit of the scan, and an encoding switch arrangement located on said bed and connected to said controls for setting the controls from the bed to adjust spatial limits of said scan regimen from said bed.

2. The system of claim 1 wherein movement of said head relative to the bed between the limits of the scan is in a longitudinal direction, and means are provided for adjusting the spatial limits of the scan in the longitudinal direction.

3. The scanning gamma camera system of claim 1 wherein said encoding switch arrangement comprises a plurality of switching elements located along the length of the bed and said controls operated responsive to the operation of certain of said switching elements along the length of the bed to limit the scan to the spatial locations denoted by said operated switching elements.

4. The scanning gamma camera system of claim 3 wherein said switching elements include with a keyboard matrix arrangement.

5. The scanning gamma camera system of claim 4 wherein:

said keyboard matrix arrangement is a crossbar matrix, said matrix having a plurality of rows and a plurality of columns, said switching elements including switches electrically located at the crossover points of said rows and columns to selectively connect rows to columns responsive to the operation of said switching elements, connecting wires for connecting said matrix to said controls to transmit a voltage from said controls to each of said rows, one of said rows receiving a zero instead of a voltage, said zero moving sequentially from row to row in a definite time frame, and said connecting wires including leads connecting said columns to said controls to define which of said switches have been operated, a limiting resistor connecting each of said columns to a voltage, said controls operated to determine the operation of each particular switch responsive to a zero in a particular time slot on a certain column, and said controls operated responsive to the determined operation of said each particular switch for setting a spatial limit on said scan.

* * * * *